US011369337B2

(12) United States Patent
Waters et al.

(10) Patent No.: US 11,369,337 B2
(45) Date of Patent: Jun. 28, 2022

(54) DETECTION OF DISTURBED BLOOD FLOW

(71) Applicant: ACIST MEDICAL SYSTEMS, INC., Eden Prairie, MN (US)

(72) Inventors: Kendall R. Waters, Livermore, CA (US); Thomas C. Moore, Livermore, CA (US)

(73) Assignee: ACIST MEDICAL SYSTEMS, INC., Eden Prairie, MN (US)

(*) Notice: Subject to any disclaimer, the term of this patent is extended or adjusted under 35 U.S.C. 154(b) by 843 days.

(21) Appl. No.: 14/966,882

(22) Filed: Dec. 11, 2015

(65) Prior Publication Data

US 2017/0164922 A1    Jun. 15, 2017

(51) Int. Cl.
| | | |
|---|---|---|
| A61B 8/06 | (2006.01) | |
| A61B 8/12 | (2006.01) | |
| A61B 8/00 | (2006.01) | |
| A61B 8/08 | (2006.01) | |
| G01S 7/52 | (2006.01) | |

(52) U.S. Cl.
CPC .............. *A61B 8/06* (2013.01); *A61B 8/12* (2013.01); *A61B 8/4461* (2013.01); *A61B 8/4483* (2013.01); *A61B 8/463* (2013.01); *A61B 8/467* (2013.01); *A61B 8/488* (2013.01); *A61B 8/5207* (2013.01); *A61B 8/5223* (2013.01); *G01S 7/52036* (2013.01); *A61B 8/0891* (2013.01); *A61B 8/4254* (2013.01); *A61B 8/445* (2013.01)

(58) Field of Classification Search
CPC ........... A61B 8/0891; A61B 8/06; A61B 8/12; A61B 8/4461; A61B 8/4483; A61B 8/463; A61B 8/467; A61B 8/488; A61B 8/5207; A61B 8/5223; A61B 8/4254; A61B 8/445; G01S 7/52036; G16H 50/30
See application file for complete search history.

(56) References Cited

U.S. PATENT DOCUMENTS

| | | |
|---|---|---|
| 3,918,025 A | 11/1975 | Koshikawa et al. |
| 4,347,443 A | 8/1982 | Whitney |

(Continued)

FOREIGN PATENT DOCUMENTS

| | | |
|---|---|---|
| CN | 101208045 A | 6/2008 |
| CN | 103025247 A | 4/2013 |

(Continued)

OTHER PUBLICATIONS

International Patent Application No. PCT/US2016/065313, International Search Report & Written Opinion dated Mar. 20, 2017, 16 pages.

(Continued)

*Primary Examiner* — Serkan Akar
(74) *Attorney, Agent, or Firm* — Fredrikson & Byron, P.A.

(57) ABSTRACT

Methods and systems are disclosed for detecting a region of disturbed blood flow within a blood-filled lumen and indicating the region of disturbed blood flow using a disturbed blood flow indicator. The region of disturbed blood flow can be detecting by processing a plurality of data vectors acquired by an imaging device. The plurality of data vectors can also be processed to generate an intravascular image. The intravascular image can be displayed to include the disturbed blood flow indicator at a region on the displayed image corresponding to a detected region of disturbed blood flow.

9 Claims, 11 Drawing Sheets

(56) References Cited

U.S. PATENT DOCUMENTS

| | | |
|---|---|---|
| 4,850,363 A | 7/1989 | Yanagawa |
| 4,860,758 A | 8/1989 | Yanagawa et al. |
| 4,949,310 A | 8/1990 | Smith et al. |
| 5,070,734 A | 12/1991 | Kawabuchi et al. |
| 5,070,735 A | 12/1991 | Reichert et al. |
| 5,131,396 A | 7/1992 | Ishiguro et al. |
| 5,183,048 A | 2/1993 | Eberle |
| 5,203,338 A | 4/1993 | Jang |
| 5,363,849 A | 11/1994 | Suorsa et al. |
| 5,396,285 A | 3/1995 | Hedberg et al. |
| 5,453,575 A | 9/1995 | O'Donnell et al. |
| 5,462,057 A | 10/1995 | Hunt et al. |
| 5,531,679 A | 7/1996 | Schulman et al. |
| 5,690,115 A | 11/1997 | Feldman et al. |
| 5,741,552 A | 4/1998 | Takayama et al. |
| 5,795,296 A | 8/1998 | Pathak et al. |
| 5,833,615 A | 11/1998 | Wu et al. |
| 5,848,969 A | 12/1998 | Panescu et al. |
| 5,876,343 A | 3/1999 | Teo et al. |
| 5,885,218 A | 3/1999 | Teo et al. |
| 5,921,931 A | 7/1999 | O'Donnell et al. |
| 6,015,385 A | 1/2000 | Finger et al. |
| 6,036,650 A | 3/2000 | Wu et al. |
| 6,095,976 A | 8/2000 | Nachtomy et al. |
| 6,132,374 A | 10/2000 | Hossack et al. |
| 6,139,501 A | 10/2000 | Roundhill et al. |
| 6,154,572 A | 11/2000 | Chaddha |
| 6,216,025 B1 | 4/2001 | Kruger |
| 6,277,075 B1 | 8/2001 | Torp et al. |
| 6,561,980 B1 | 5/2003 | Gheng et al. |
| 6,589,181 B2 | 7/2003 | Grunwald et al. |
| 6,645,147 B1 | 11/2003 | Jackson et al. |
| 6,771,803 B1 | 8/2004 | Turek et al. |
| 7,194,294 B2 | 3/2007 | Panescu et al. |
| 7,691,061 B2 | 4/2010 | Hirota |
| 7,925,064 B2 | 4/2011 | Cloutier et al. |
| 9,292,918 B2 | 3/2016 | Zagrodosky et al. |
| 9,858,668 B2 | 1/2018 | Jones et al. |
| 10,089,755 B2 | 10/2018 | Griffin et al. |
| 10,231,712 B2 | 3/2019 | Ebbini et al. |
| 10,258,304 B1 | 4/2019 | Kiraly et al. |
| 10,278,670 B2 | 5/2019 | Ohuchi et al. |
| 10,383,602 B2 | 8/2019 | Cho et al. |
| 10,542,954 B2 | 1/2020 | Spencer et al. |
| 2001/0017941 A1 | 8/2001 | Chaddha |
| 2001/0029336 A1 | 10/2001 | Teo |
| 2003/0015037 A1 | 1/2003 | Stephans et al. |
| 2003/0055334 A1 | 3/2003 | Steinbacher et al. |
| 2003/0063787 A1 | 4/2003 | Natanzon et al. |
| 2003/0078497 A1 | 4/2003 | Ji et al. |
| 2003/0097069 A1 | 5/2003 | Avinash et al. |
| 2003/0103212 A1 | 6/2003 | Westphal et al. |
| 2003/0191392 A1 | 10/2003 | Haldeman |
| 2003/0208123 A1 | 11/2003 | Panescu |
| 2004/0030250 A1 | 2/2004 | Stewart |
| 2004/0037164 A1 | 2/2004 | Garlick et al. |
| 2004/0199047 A1 | 10/2004 | Taimisto et al. |
| 2005/0119573 A1* | 6/2005 | Vilenkin ............ A61B 5/02007 600/450 |
| 2005/0215897 A1 | 9/2005 | Sakaguchi et al. |
| 2005/0249391 A1 | 11/2005 | Kimmel et al. |
| 2006/0253028 A1 | 11/2006 | Lam et al. |
| 2007/0016046 A1* | 1/2007 | Mozayeni ............ A61B 8/0808 600/443 |
| 2007/0016068 A1 | 1/2007 | Grunwald et al. |
| 2007/0036404 A1 | 2/2007 | Li |
| 2007/0100239 A1 | 5/2007 | Nair et al. |
| 2007/0167710 A1 | 7/2007 | Unal et al. |
| 2007/0201736 A1 | 8/2007 | Klingensmith et al. |
| 2008/0015569 A1 | 1/2008 | Saadat et al. |
| 2008/0031498 A1 | 2/2008 | Corcoran et al. |
| 2008/0043024 A1 | 2/2008 | Schiwietz et al. |
| 2008/0075375 A1 | 3/2008 | Unal |
| 2008/0177183 A1 | 7/2008 | Courtney et al. |
| 2008/0200815 A1 | 8/2008 | Van Der Steen et al. |
| 2008/0234582 A1 | 9/2008 | Nair et al. |
| 2009/0088830 A1 | 4/2009 | Mohamed et al. |
| 2009/0105579 A1* | 4/2009 | Garibaldi ............ G06T 7/38 600/409 |
| 2009/0284332 A1 | 11/2009 | Moore et al. |
| 2010/0010344 A1 | 1/2010 | Ahn et al. |
| 2010/0094127 A1 | 4/2010 | Xu |
| 2010/0174190 A1 | 7/2010 | Hancock et al. |
| 2010/0312092 A1 | 12/2010 | Listz et al. |
| 2010/0312109 A1 | 12/2010 | Satoh |
| 2011/0071404 A1 | 3/2011 | Schmitt et al. |
| 2011/0160586 A1 | 6/2011 | Li et al. |
| 2011/0182517 A1 | 7/2011 | Farsiu et al. |
| 2011/0196237 A1* | 8/2011 | Pelissier ............ A61B 8/467 600/454 |
| 2011/0257527 A1 | 10/2011 | Suri |
| 2012/0022360 A1 | 1/2012 | Kemp |
| 2012/0065511 A1 | 3/2012 | Jamello, III |
| 2012/0123271 A1 | 5/2012 | Cai |
| 2012/0170848 A1 | 7/2012 | Kemp et al. |
| 2012/0224751 A1 | 9/2012 | Kemp et al. |
| 2013/0109968 A1 | 5/2013 | Azuma |
| 2013/0296693 A1* | 11/2013 | Wenzel ............ A61B 5/061 600/424 |
| 2013/0303907 A1 | 11/2013 | Corl |
| 2013/0303910 A1 | 11/2013 | Hubbard et al. |
| 2013/0317359 A1 | 11/2013 | Wilson et al. |
| 2014/0099011 A1 | 4/2014 | Begin |
| 2014/0100440 A1 | 4/2014 | Cheline et al. |
| 2014/0180078 A1 | 6/2014 | Nair |
| 2014/0257087 A1 | 9/2014 | Elbasiony et al. |
| 2014/0268167 A1 | 9/2014 | Friedman et al. |
| 2014/0270445 A1 | 9/2014 | Kemp |
| 2014/0276065 A1 | 9/2014 | He et al. |
| 2014/0316758 A1* | 10/2014 | Yagi ............ A61B 34/25 703/9 |
| 2014/0350404 A1 | 11/2014 | Nikhil et al. |
| 2014/0355850 A1 | 12/2014 | Kelm et al. |
| 2015/0073279 A1 | 3/2015 | Cai et al. |
| 2015/0099975 A1 | 4/2015 | Lam et al. |
| 2015/0141832 A1 | 5/2015 | Yu et al. |
| 2015/0235360 A1 | 8/2015 | Zheng et al. |
| 2015/0245776 A1* | 9/2015 | Hirohata ............ A61B 5/026 600/504 |
| 2015/0356734 A1 | 12/2015 | Ooga et al. |
| 2016/0007967 A1 | 1/2016 | Johnson et al. |
| 2016/0022248 A1 | 1/2016 | Mori et al. |
| 2016/0206290 A1 | 7/2016 | Itoh et al. |
| 2016/0300350 A1 | 10/2016 | Choi et al. |
| 2017/0100100 A1 | 4/2017 | Jamello et al. |
| 2017/0119242 A1 | 5/2017 | Jia et al. |
| 2017/0164825 A1 | 6/2017 | Chen et al. |
| 2017/0178325 A1 | 6/2017 | Ye et al. |
| 2017/0193658 A1 | 7/2017 | Cardinal et al. |
| 2017/0224286 A1 | 8/2017 | Sakamoto |
| 2017/0301089 A1 | 10/2017 | Lam et al. |
| 2017/0330331 A1 | 11/2017 | Bhatt et al. |
| 2018/0042575 A1 | 2/2018 | Moore et al. |
| 2020/0082525 A1 | 3/2020 | Xu et al. |
| 2020/0226422 A1 | 7/2020 | Shimin et al. |
| 2020/0320659 A1 | 10/2020 | Whiting et al. |

FOREIGN PATENT DOCUMENTS

| | | |
|---|---|---|
| EP | 346889 B1 | 1/1995 |
| EP | 851241 A2 | 7/1998 |
| EP | 1387317 A1 | 2/2004 |
| EP | 1609423 A2 | 12/2005 |
| EP | 1988505 A1 | 11/2008 |
| EP | 2488107 A2 | 8/2012 |
| JP | 62221335 A | 9/1987 |
| JP | H09-000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007512862 A | 5/2007 |

(56) References Cited

FOREIGN PATENT DOCUMENTS

| JP | 2007175542 A | | 7/2007 | | |
|---|---|---|---|---|---|
| JP | 2007229015 A | | 9/2007 | | |
| JP | 2008508970 A | | 3/2008 | | |
| JP | 2008536638 A | | 9/2008 | | |
| JP | 2009504329 A | | 2/2009 | | |
| JP | 2009545406 A | | 12/2009 | | |
| JP | 4648652 B2 | | 3/2011 | | |
| JP | 2012090819 A | | 5/2012 | | |
| JP | 2013507227 A | | 3/2013 | | |
| JP | 2004081386 A | | 3/2018 | | |
| WO | 0101864 A1 | | 1/2001 | | |
| WO | 2006015877 A1 | | 2/2006 | | |
| WO | WO 2006/102511 | * | 9/2006 | ............... | A61B 5/02 |
| WO | 2006113857 A1 | | 10/2006 | | |
| WO | 2006122001 A2 | | 11/2006 | | |
| WO | 2007098209 A2 | | 8/2007 | | |
| WO | 2008016992 A1 | | 2/2008 | | |
| WO | 2008110013 A1 | | 9/2008 | | |
| WO | 2011046903 A2 | | 4/2011 | | |
| WO | 2012070588 A1 | | 5/2012 | | |
| WO | 2014186268 A1 | | 11/2014 | | |
| WO | 2017062265 A1 | | 4/2017 | | |

OTHER PUBLICATIONS

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.

Foster, "Transducer Materials and Probe Construction," Ultrasound in Medicine and Biology, vol. 26, Supp. 1, 2000, pp. S2-S5.

Frijlink et al., "High Frequency Harmonic Imaging in Presence of Intravascular Stents," IEEE Ultrasonics Symposium, 2003, pp. 208-211.

Garcia-Garcia et al., "Imaging of coronary atherosclerosis: intravascular ultrasound," European Heart Journal, vol. 3, 2010, pp. 2456-2469.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.

Smith et al., "The Maltese Cross Processor: Speckle Reduction for Circular Transducers," Ultrasonic Imaging, vol. 10, No. 3, Jul. 1988, pp. 153-170.

U.S. Appl. No. 61/218,177, titled Vector Domain Image Enhancement for Mechanically Rotating Imaging Catheters, filed Jun. 18, 2009.

Van Der Steen et al., "IVUS Harmonic Imaging," Ultrasound in Medicine and Biology, vol. 26, Supp. 2, 2000, p. A90.

Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.

Waters et al., "Development of a High-Definition Intravascular Ultrasound Imaging System and Catheter," IEEE International Ultrasonics Symposium Proceedings, Oct. 18, 2011, 4 pages.

Moore et al., "Intravascular Ultrasound Image Processing of Blood-Filled or Blood-Displaced Lumens," U.S. Appl. No. 15/704,710, filed Sep. 14, 2017, 49 pages.

* cited by examiner

DETECTION OF DISTURBED BLOOD FLOW

TECHNICAL FIELD

This disclosure relates generally to medical imaging, and more particularly to intravascular imaging of blood flow.

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, including a blood-filled lumen, coronary artery wall morphology, and devices, such as stents, at or near the coronary artery wall. Images generated using medical imaging techniques can be useful for diagnostic purposes, such as identifying diagnostically significant characteristics of a vessel.

One such diagnostically significant characteristic of a vessel, for which medical imaging techniques can assist in identifying, is the presence of particular anatomic substrates, such as plaque burden. Although medical imaging can be used to identify plaque burden, this alone is likely insufficient to predict actual plaque progression. Predicting plaque progression using medical imaging techniques can benefit from additionally detecting the presence of pro-inflammatory stimuli within the vessel. However, many current medical imaging approaches to detecting the presence of pro-inflammatory stimuli within a vessel are relatively complex, generally involving multimodality imaging (e.g., biplane angiography and intravascular ultrasound) in addition to computational fluid dynamics modeling.

SUMMARY

This disclosure in general describes a relatively simple approach that may assist medical personnel in ascertaining the presence of pro-inflammatory stimuli within a vessel. As such, this disclosure may enable wider use of hemodynamic conditions for assessment of vulnerable plaques, or those plaques that may lead to clinical events. Advantageously, the present disclosure may allow medical personnel to detect pro-inflammatory stimuli through the use of a single modality, such as an intravascular ultrasound imaging system, to provide structural and hemodynamic information without requiring extensive alteration to typical intravascular ultrasound imaging workflow.

In one example, an intravascular ultrasound imaging system can be configured to detect a region of disturbed blood flow. The intravascular ultrasound imaging system can provide an intravascular image including a disturbed blood flow indicator indicating the region of disturbed blood flow. Detecting and indicating such region of disturbed blood flow can be valuable for medical personnel in ultimately determining a pro-inflammatory site within the vessel.

Data vectors acquired using an imaging device, such as an ultrasound transducer, can be processed to detect a region of disturbed blood flow. Detection of disturbed blood flow can be accomplished in a variety of ways, either alternatively or in conjunction with one another. For example, processing the data vectors to detect a region of disturbed blood flow can include calculating interference between a first data vector and a second data vector. The calculated interference between the first data vector and the second data vector can include, in some embodiments, a degree of phase cancellation between the first and second data vectors and/or a degree of wavelength shift (e.g., a half-wavelength shift) of at least a portion of a data vector.

As another example, processing the data vectors to detect a region of disturbed blood flow can include comparing a first portion of the first data vector to a second portion of the second data vector to determine a difference between the respective first and second portions. The difference between the respective first and second portions may, in some embodiments, be equal to or greater than a predetermined threshold for a region of disturbed blood flow to be detected. In some embodiments, the predetermined threshold can correspond to a predetermined degree to which the second portion of the second data vector is time shifted.

As a further example, processing the data vectors to detect a region of disturbed blood flow can include generating speckle density values for respective regions within a blood-filled lumen. The generated speckle density values can be compared to calculate a difference. In some embodiments, the region of disturbed blood flow can be detected to correspond to a particular region within the blood-filled lumen when the calculated speckle density difference is equal to or greater than a predetermined threshold.

In addition, processing the data vectors to detect a region of disturbed blood flow can include detecting blood movement within the blood-filled lumen in a generally radial direction relative to the longitudinal axis of the catheter and/or ultrasound transducer. Moreover, processing the data vectors to detect a region of disturbed blood flow can include, additionally or alternatively, detecting non-laminar blood flow within the blood-filled lumen. Also, processing the data vectors to detect a region of disturbed blood flow can include, additionally or alternatively, detecting blood flow that is not generally parallel to the vessel walls.

Where a region of disturbed blood flow is detected, an image can be displayed having a disturbed blood flow indicator indicating the region of disturbed blood flow on the image. In various embodiments, the disturbed blood flow indicator can be displayed on the image so as to distinguish the disturbed blood flow indicator, and thus the region of disturbed blood flow, from other portions of the displayed image.

Embodiments also include a non-transitory computer-readable storage article having computer-executable instructions stored thereon to cause at least one programmable processor to receive imaging data (e.g., a plurality of data vectors) representing one or more items in an imaging view. Such instructions can also cause the processor to determine a region of disturbed blood flow within the blood-filled lumen based on the imaging data, for instance by using one or more techniques described above. In addition, the instructions can cause the processor to convey an intravascular image for outputting on a display. The intravascular image can include a disturbed blood flow indicator located at the determined region of disturbed blood flow.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description.

Examples of the present invention will hereinafter be described in conjunction with the appended drawings.

DETAILED DESCRIPTION

The following detailed description is exemplary in nature and is not intended to limit the scope, applicability, or configuration of the invention in any way. Rather, the following description provides some practical illustrations for implementing examples of the present invention. Those skilled in the art will recognize that many of the noted examples have a variety of suitable alternatives.

Figure 1:
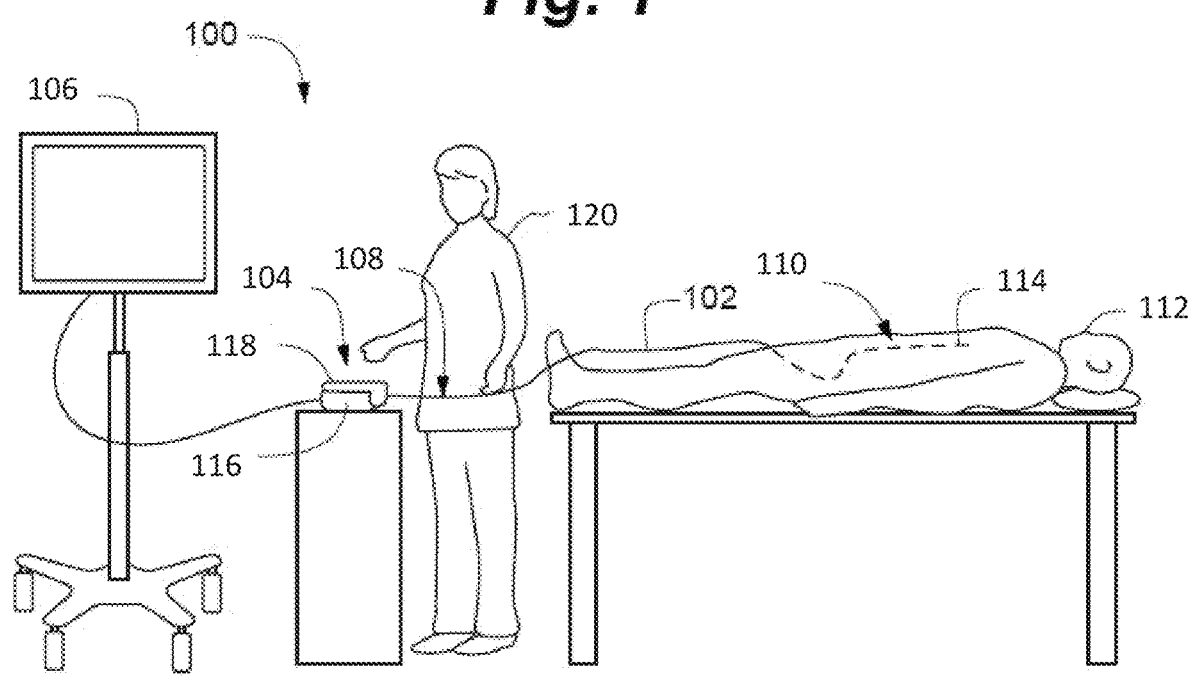
FIG. 1 is an illustrative example of a system configured to perform intravascular imaging.

FIG. 1 illustrates an example of a system 100 that may be configured to perform intravascular imaging. System 100 can include a catheter assembly 102, a translation device 104, and an imaging engine 106. The catheter assembly 102 may include a proximal end 108 and a distal end 110 configured to be inserted into a vessel of a patient 112. In one example, catheter assembly 102 may be inserted into the patient 112 via the femoral artery and guided to an area of interest within the patient 112. The broken lines in FIG. 1 represent portions of catheter assembly 102 within the patient 112.

In some examples, the catheter assembly 102 can include an intravascular imaging device 114 configured to generate imaging data. Intravascular imaging device 114 can be in communication with imaging engine 106. In some embodiments, intravascular imaging device 114 is an ultrasound transducer configured to emit and receive ultrasound energy and generate ultrasound imaging data. The image data generated by the imaging device 114 can represent a cross-section of an area of interest within the patient 112 at the location of the imaging device 114. The image data generally will represent a plurality of image items at the cross-sectional location of the imaging device 114, such as, for example, blood, various layers of a vessel of the patient 112, and/or any accumulated matter within the vessel (e.g., plaque).

The translation device 104 can be configured to translate intravascular imaging device 114 of catheter assembly 102. The translation device 104 may comprise a linear translation system (LTS) 116. The LTS 116 may be mechanically engaged with catheter assembly 102 and configured to translate the catheter assembly 102 a controlled distance within the patient 112 during a translation operation, for example a pullback or push-forward operation. The system 100 may comprise a patient interface module (PIM) 118 configured to interface the translation device 104 with the catheter assembly 102. Translating the imaging device 114 can allow for cross-sectional image data to be collected at various longitudinal locations within a vessel of the patient 112. This cross-sectional image data at various longitudinal locations can then be compiled, in some applications, to generate a longitudinal cross-sectional image of an area of interest.

The imaging engine 106 can be in communication with intravascular imaging device 114 and translation device 104. According to some examples, the imaging engine 106 may comprise at least one programmable processor. In some examples, the imaging engine 106 may comprise a computing machine including one or more processors configured to receive commands from a system user 120 and/or display data acquired from catheter assembly 102 via a user interface. The computing machine may include computer peripherals (e.g., keyboard, mouse, electronic display) to receive inputs from the system user 120 and output system information and/or signals received from catheter assembly 102 (e.g., rendered images). In some examples, the user interface of the computing machine may be a touchscreen display configured to act as both an input device and an output device. In some examples, imaging engine 106 may include memory modules for storing instructions, or software, executable by the one or more processors.

Figure 2:
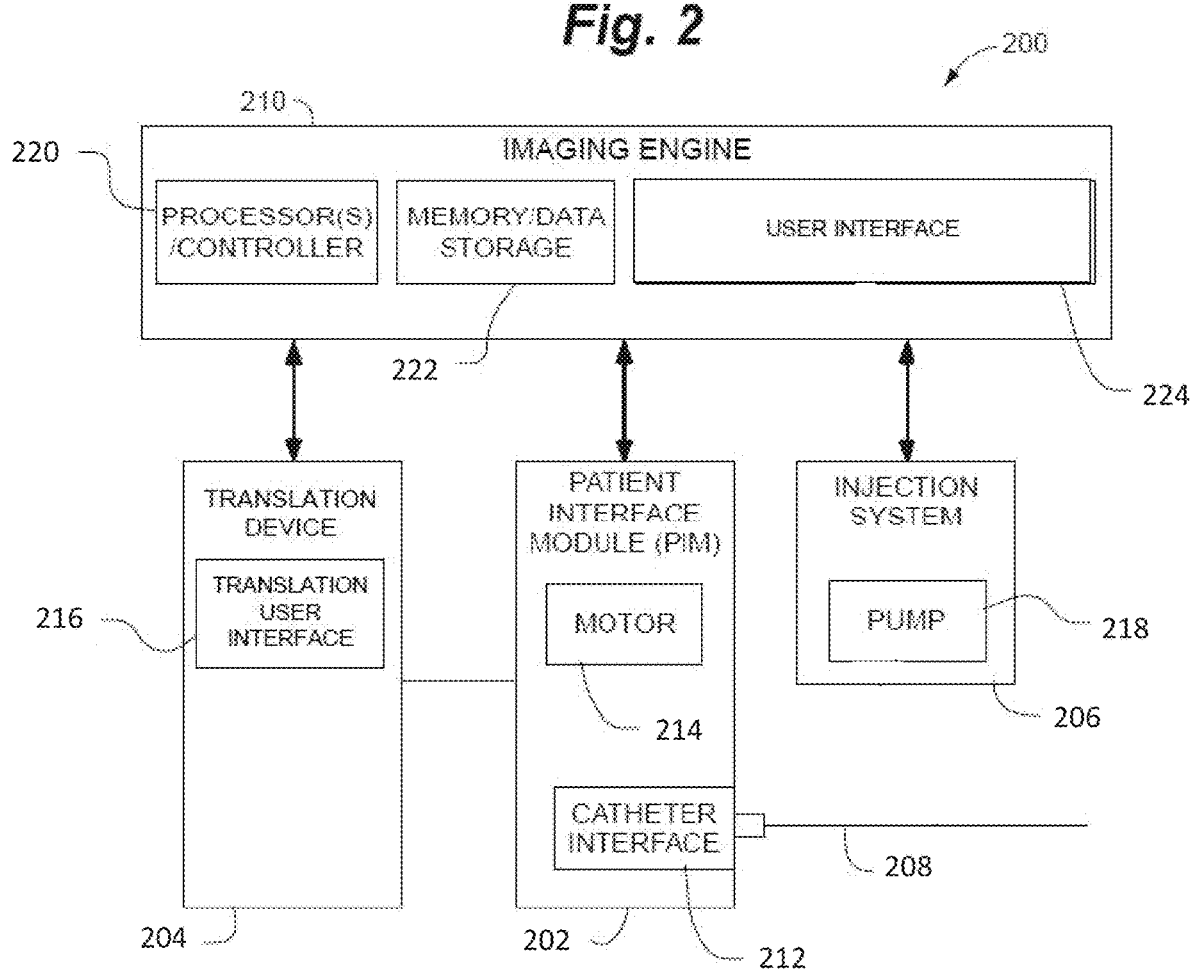
FIG. 2 is a block diagram illustrating an exemplary system configured to perform intravascular imaging.

FIG. 2 is a block diagram illustrating an exemplary system 200 adapted to perform intravascular imaging. The system 200 can include PIM 202, translation device 204, injection system 206, catheter assembly 208, and imaging engine 210. The system 200 can be configured to be used with an intravascular ultrasound imaging device, such as that described with respect to FIG. 1.

PIM 202 can provide an electromechanical interface between catheter assembly 208 and imaging engine 210. In some embodiments, PIM 202 may provide a catheter interface 212 to secure catheter assembly 208 to the system 200. The PIM 202 may include a motor 214 configured to provide mechanical energy to rotate an intravascular imaging device (e.g., ultrasound transducer) of catheter assembly 208. According to various examples, PIM 202 may provide an electrical interface that transmits signals from the intravascular imaging device of catheter assembly 208 and receives return signals.

Translation device 204 can be configured to provide longitudinal translation of catheter assembly 208. Translation device 204 may comprise a linear translation system (LTS). The translation device 204 may be configured to mate with PIM 202 and catheter assembly 208 to enable controlled pullback of an intravascular imaging device of catheter assembly 208. According to some examples, the translation device 204 may feature a translation user interface 216 which may comprise a translation display configured to display translation data associated with the translation of the intravascular imaging device to a user of the system 200. In some embodiments, translation data may include linear distance traversed and/or translation speed. The translation user interface 216 may be configured to receive inputs from a user to control starting/stopping translation, setting translation speed, resetting linear distance traversed to zero, and/or switching to manual mode. In manual mode, a user may freely move the intravascular imaging device of the catheter assembly forward and backward (e.g., distally and proximally within a vessel). In some examples, the translation device 204 may be configured to enable both pullback and push-forward of the intravascular imaging device at a controlled rate. In another example, the translation device 204 may be configured to oscillate, or cycle, the intravascular imaging device by alternately performing pullback and push-forward operations. In some examples, the translation device 204 may include a position sensor configured to measure a distance of a translation operation.

The injection system 206 can be configured to deliver fluid into a vessel of a patient. Although, in some embodiments the system 200 may not include the injection system 206. The injection system 206, when present in the system 200, may comprise an injector pump 218 configured to deliver one or more fluids (e.g., contrast and/or saline) into the patient. In some examples, the injector pump 218 may be automated, in electrical communication with, and controlled by imaging engine 210. According to some examples, injector pump 218 may comprise a manual pump (e.g., syringe injection) configured to allow a user to manually deliver one or more fluids into the patient. In one example, the injector pump 218 may be in fluid communication with an intravascular blood displacement fluid port, which may be associated with catheter assembly 208, such that fluid from the injection system 206 is delivered into a patient's vasculature via the intravascular blood displacement fluid port. In another example, the injector pump 218 may be in fluid communication with a guide catheter (e.g., a guide catheter through which an embodiment of the catheter assembly 208 is passed through), which can have an intravascular blood displacement fluid port defined therein. Various other configurations can be used as appropriate when it is desired to deliver fluid into a vessel using injection system 206. As can be appreciated, the injection system 206 may be configured to deliver any number of fluids and any quantity of fluid as appropriate for a specific application of the system 200. In some examples, the quantity of blood displacement fluid may comprise a contrast media or saline.

The imaging engine 210, in the illustrated example, includes one or more programmable processors 220, memory/data storage component 222 which can be in communication with the one or more programmable processors 220, and a user interface 224 which can be in communication with the one or more programmable processors 220 and/or the memory/storage component 222. The imaging engine 210 can itself be in communication with the translation device 204, PIM 202, and/or injection system 206 (when present). The user interface 224 can include a display for outputting an image generated based on image data acquired by the catheter assembly 208 (e.g., an ultrasound transducer of the catheter assembly). Before the image is output on the display of the user interface 224, image data acquired by the catheter assembly 208 can undergo one or more image processing techniques at the imaging engine 210. For instance, the memory/data storage component 222 can include instructions, or software, for performing one or more image processing techniques and the one or more processors 220 may execute the image processing techniques based on the instructions.

Figure 3:
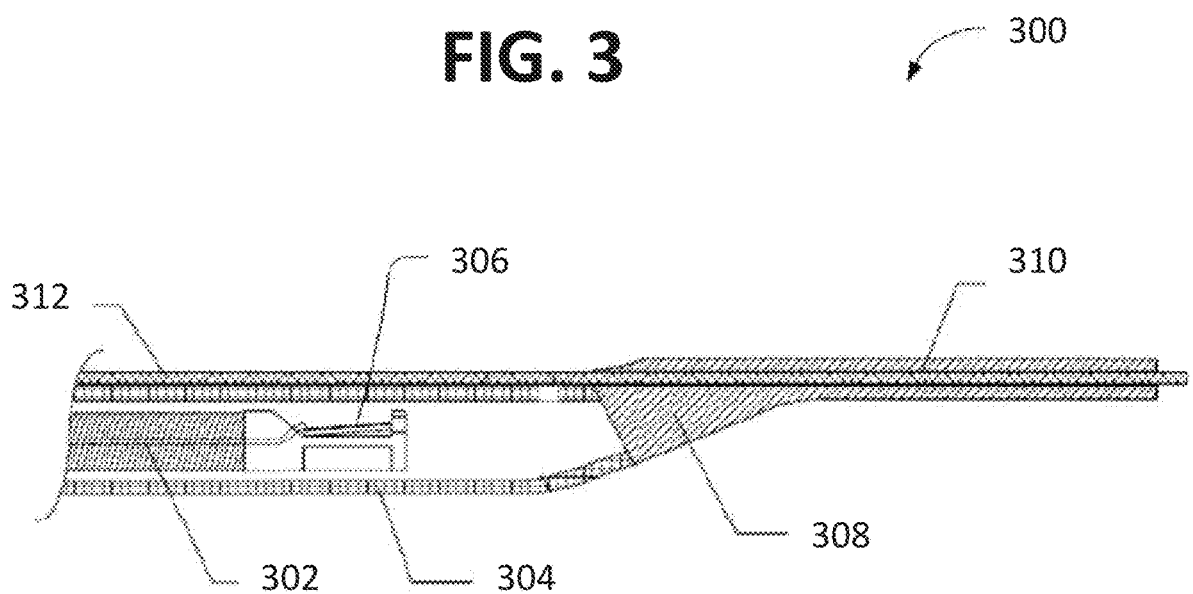
FIG. 3 is a side cross-sectional view of an embodiment of a portion of a catheter assembly.

FIG. 3 shows a side cross-sectional view of an embodiment of a distal portion of a catheter assembly 300, which can be used in the systems described previously with respect to FIGS. 1 and 2. The catheter assembly 300 may include a drive cable 302, a sheath 304, and an ultrasound transducer 306. As noted above, the drive cable may be coupled to a PIM to rotate the drive cable 302 within the sheath 304. The ultrasound transducer 306 may be coupled to the drive cable 302 such that rotation and/or translation of the drive cable 302 causes the ultrasound transducer 306 to rotate and/or translate within sheath 304. The ultrasound transducer 306 may be configured to emit and receive acoustic energy during rotation and/or translation to generate ultrasound data. In some examples, the catheter assembly 300 may also include an imaging window (not shown) substantially transparent to the frequency of the acoustic energy emitted by the ultrasound transducer 306. The catheter assembly 300 may also include a distal end 308 forming a guidewire lumen 310 configured to accept a guidewire 312 to guide the catheter assembly 300 into a vessel of a patient and/or translate the catheter assembly 300 within the vessel.

Figure 4:
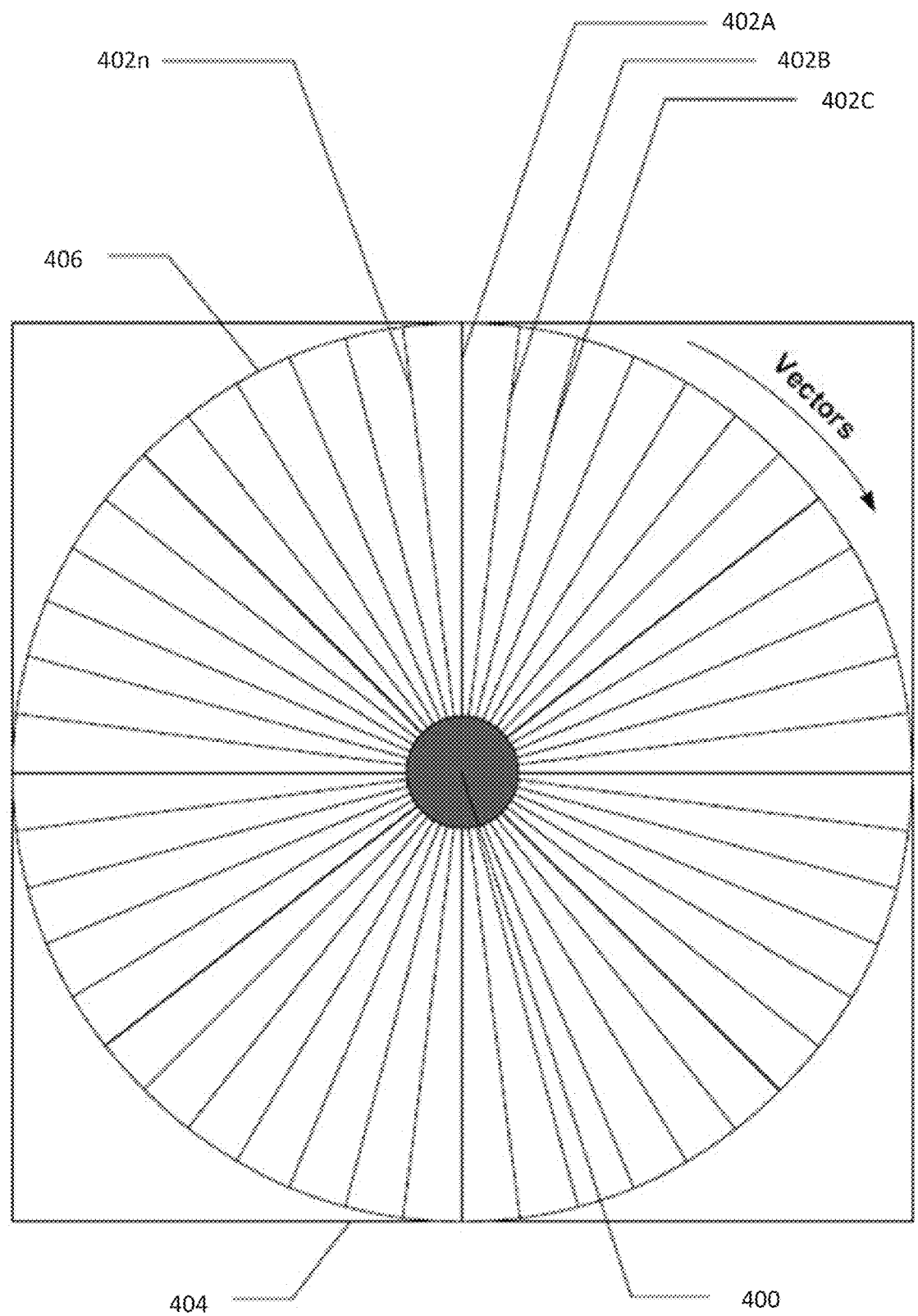
FIG. 4 is a front view of an embodiment of a catheter including data vectors propagated by a transducer of the catheter.

FIG. 4 illustrates a front view of propagating ultrasound data vectors of a catheter 400. In this example, the catheter 400 may be a mechanically rotating ultrasound imaging catheter similar to catheters previously described. Likewise, the catheter 400 may be configured to rotate an ultrasound transducer (not shown) relative to a sheath of the catheter 400, and the ultrasound transducer may be configured to generate ultrasound data by emitting and receiving acoustic energy. The ultrasound data vectors illustrated in FIG. 4 are indicative of acoustic energy emitted and received by the ultrasound transducer at different rotational positions. More specifically, each data vector is representative of ultrasound data collected by the ultrasound transducer at different rotational positions of the ultrasound transducer. Each of the data vectors can, in some embodiments, be acquired at different times.

As shown in FIG. 4, the ultrasound transducer of catheter 400 may generate ultrasound data on a vector-by-vector basis as the transducer is rotated. For example, the ultrasound transducer may initially acquire an ultrasound data vector 402A and continue to acquire vectors 402B through 402n as the ultrasound transducer is rotated clockwise. Accordingly, vectors 402A-402n can be representative of a full 360 degree rotation of the ultrasound transducer within a vessel and make up a single frame. The number of data vectors acquired per rotation may vary depending on the application of the catheter 400. For instance, in some embodiments, the catheter is configured to generate between about 500 and about 5000 vectors per rotation. For example, in an embodiment generating 512 vectors per rotation (e.g., frame) the angle between data vectors may then be characterized as approximately $2\pi/512$ radians or 360/512 degrees. In an example of a catheter configured to generate 4096 vectors per rotation (e.g., frame), the angle between data vectors may be approximately $2\pi/4096$ radians or 360/4096 degrees. FIG. 4 also provides a representation of a data frame 404 that comprises emitted and received vectors 402A-402n. A field of view 406 of the catheter 400 may be based on the magnitude of the data vectors propagated by the catheter and may vary to suit a specific application. The magnitude of the data vectors may be based on a number of factors, for example, the frequency of the emitted wave (e.g., 60 MHz) and/or the power level of the wave. In some embodiments, the ultrasound transducer of catheter 400 can emit acoustic energy at differing frequencies within the single frame 404.

Figure 5A:
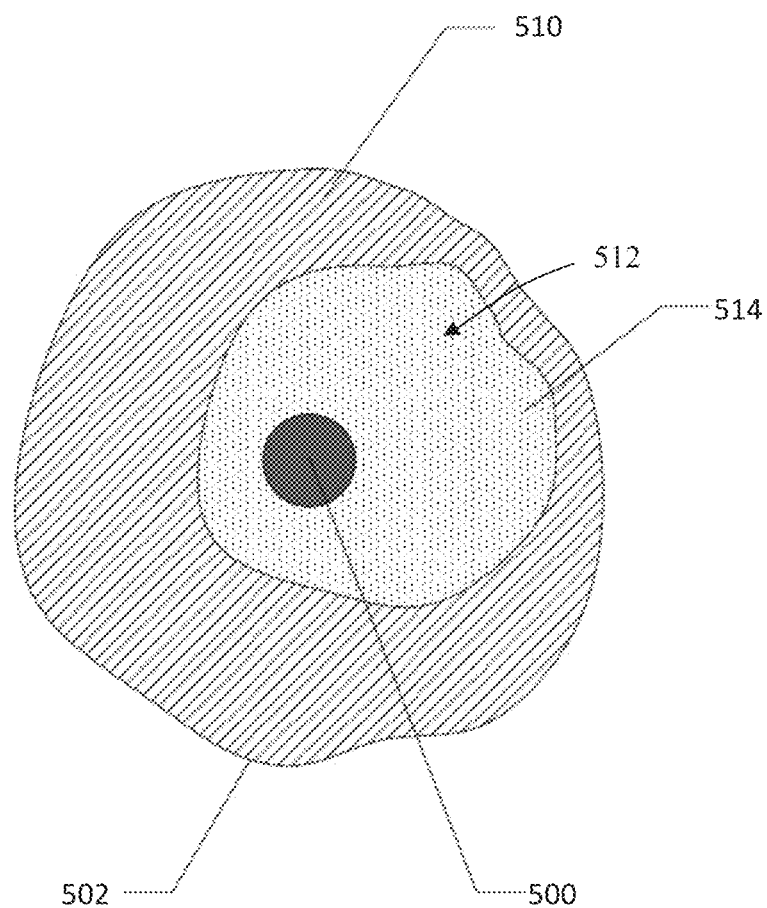
FIGS. 5A and 5B are transverse and longitudinal cross-sectional views, respectively, of an embodiment of a catheter in a blood-filled lumen.
Figure 5B:
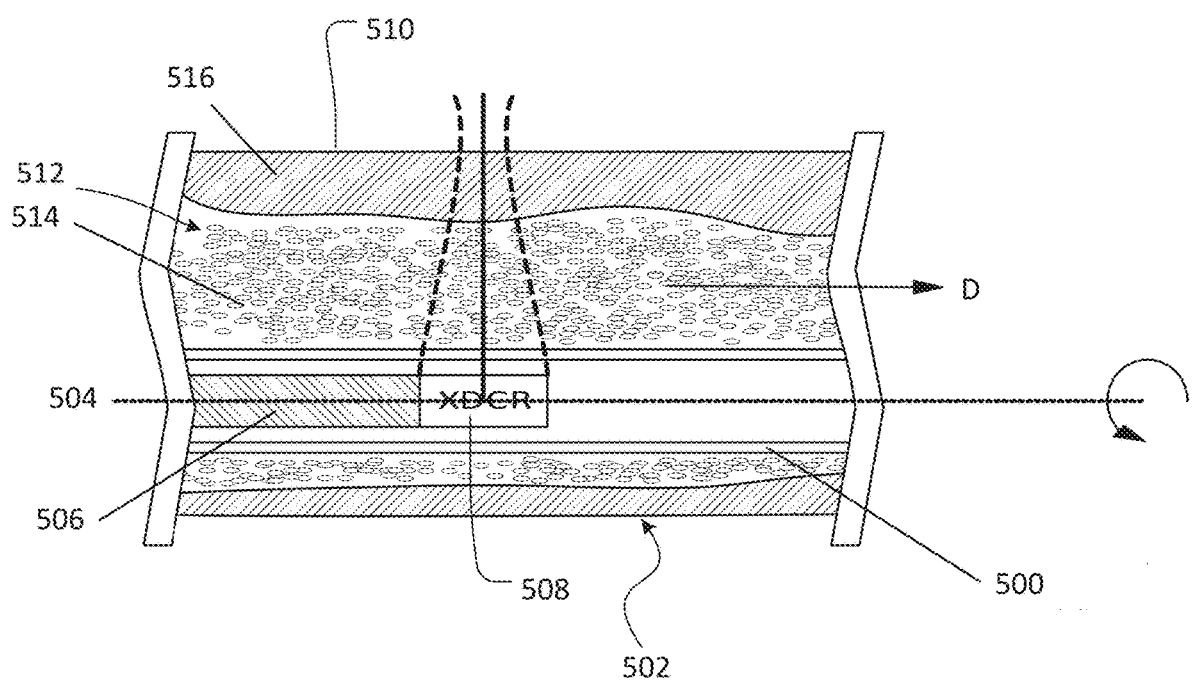

FIGS. 5A and 5B show examples of transverse and longitudinal cross-sectional views, respectively, of an embodiment of a catheter 500 in a vessel 502. The catheter 500 defines a longitudinal axis 504 and has an imaging core 506 including ultrasound transducer 508 (shown in FIG.

5B). As noted above, the catheter 500 may be directly guided into the vessel 502 or, in certain examples, be guided into the vessel 502 via a guide wire.

The vessel 502 may be a vessel of a vascular system of a patient, such as a coronary artery, including a vessel wall 510 defining a vessel lumen 512 through which blood 514 flows. As such, the vessel lumen 512 as shown is a blood-filled lumen. In addition to blood 514, the vessel lumen 512 may also include, in various applications, one or more plaque components 516 (shown in FIG. 5B) that have accumulated on the vessel wall 510 within the vessel lumen 512 over time. The extent of plaque buildup within the vessel 502 can correspond to the extent to which the vessel 502 is diseased (e.g., the narrower the vessel lumen 512 is as a function of plaque component 516 accumulation, the more diseased the vessel 502 is). Such plaque components 516 can include, for instance, atherosclerotic plaque such as lipids.

The vessel 502 is a relatively non-diseased vessel, lacking extensive plaque buildup and defining a generally constant vessel lumen 512 diameter along the longitudinal direction of the vessel 502. As shown in FIG. 5B, the blood 514 can exhibit generally laminar flow within the vessel lumen 512 in a direction D when the vessel 502 is a relatively non-diseased vessel. Laminar blood flow within vessel lumen 512 in the direction D can be predominantly parallel to the vessel walls 510. Accordingly, where the catheter 500 is oriented within the vessel 502 parallel to the vessel walls 510 as shown here, laminar blood flow within the vessel lumen 512 in the direction D can be generally parallel to the catheter longitudinal axis 504.

Figure 6:
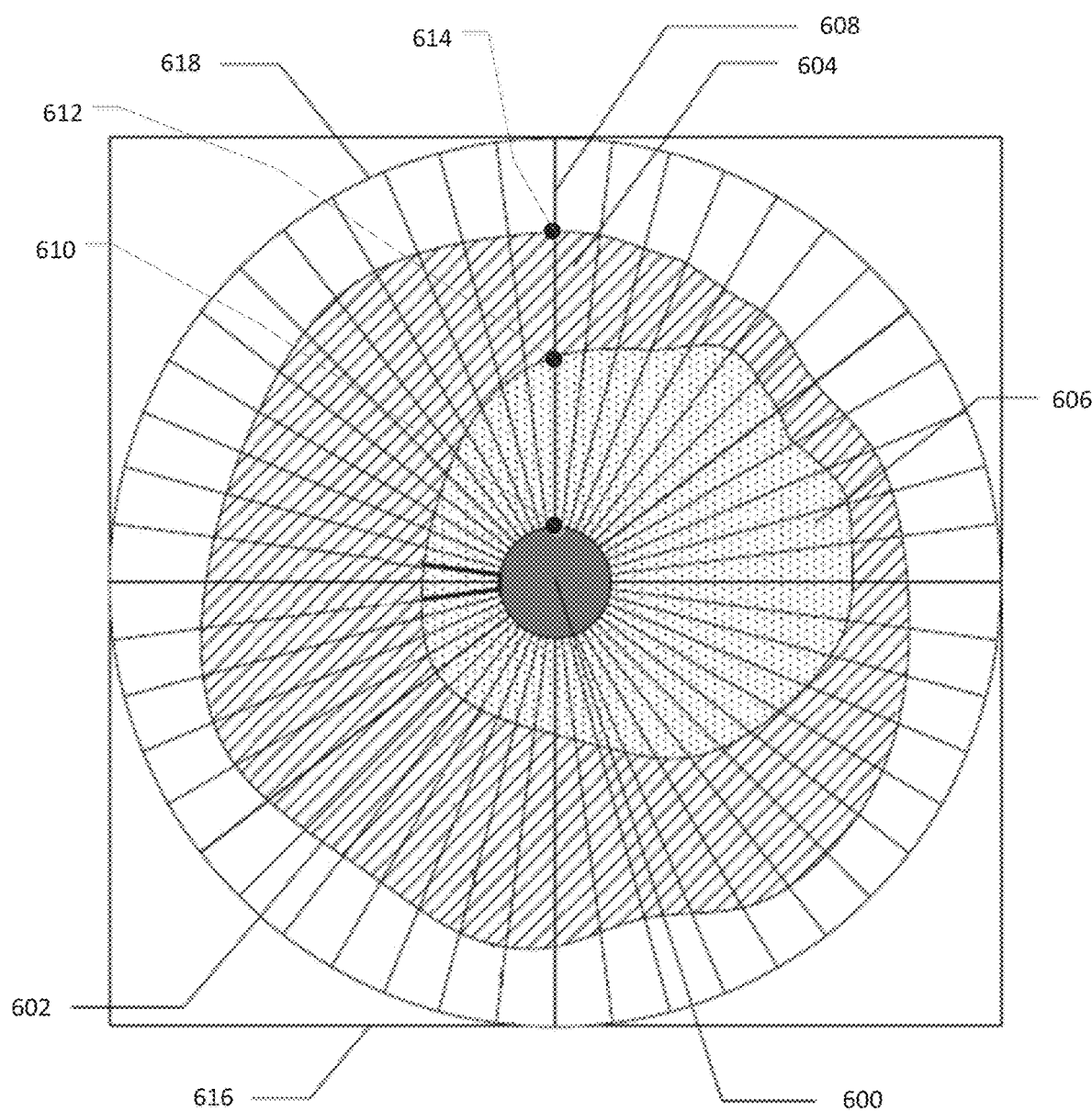
FIG. 6 is a cross-sectional view of an embodiment of a catheter in a vessel lumen including data vectors propagated by the catheter.

FIG. 6 shows a cross-sectional view of a catheter 600 within a vessel 602 and an overlay of ultrasound data vectors propagated by the catheter 600. Vessel 602 is similar to the vessel described previously with respect to FIGS. 5A and 5B and catheter 600 is similar to the catheters described previously. As in those examples, the catheter 600 may include an ultrasound transducer configured to generate ultrasound data in the form of a plurality of data vectors. In this example, each data vector corresponds to ultrasound data collected by emitting acoustic energy and receiving a reflection of the energy, or backscatter, from vessel 602 and/or items of or within vessel 602. Different portions of the vessel, for example vessel wall 604 as well as fluid (e.g. blood) and plaque in vessel lumen 606, are likely to have different material compositions. The different material compositions of the different portions of the vessel can result in different responses to the emitted acoustic energy. The different responses of the various portions can be exploited in many embodiments to distinguish different portions, or regions of interest, of the vessel and in turn provide a more diagnostically valuable image.

For instance, variations in ultrasound backscatter levels along a data vector may be used to determine the boundary between the lumen 606 and the vessel wall 604. For example, vessel wall 604 and the fluid within vessel lumen 606 (e.g., blood) may reflect varying amounts of acoustic energy emitted by the ultrasound transducer of catheter 600. Accordingly, the ultrasound data collected along a data vector may capture the variation in the ultrasound backscatter level between the vessel wall 604 and the vessel lumen 606. For example, a first region of data vector 608 between data points 610 and 612 may have a backscatter level consistent with blood flowing within the vessel lumen 606 while a second region of data vector 608 between data points 612 and 614 may have a backscatter level consistent with vessel wall 604. Further, the transition between the backscatter levels of the first region and the second region may be used to identify the boundary between the vessel wall 604 and the vessel lumen 606, located approximately at data point 612. As noted above, data frame 616 may comprise data vectors acquired during a full 360 degree rotation of the ultrasound transducer of catheter 600. As such, data frame 616 can include imaging data at a cross-section of the vessel 602 within an imaging view 618 that is defined by the particular imaging parameters used in a specific application.

Figure 7:
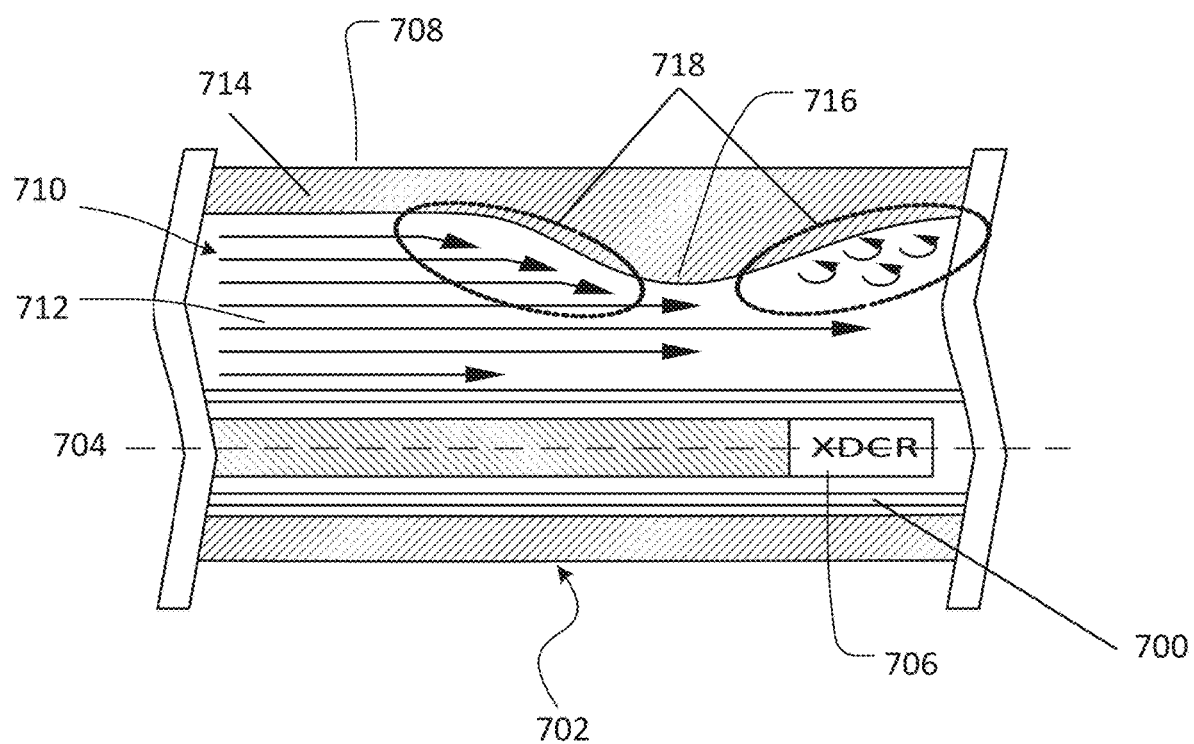
FIG. 7 is a longitudinal cross-sectional view of an exemplary blood-filled lumen having regions of disturbed blood flow.

In some instances, the hemodynamics of blood flow within the vessel lumen can impact the backscatter of acoustic energy received at the ultrasound transducer. This can be the case, for example, when imaging a portion of a vessel that is diseased. At such a vessel portion, blood movement in a radial direction relative to a longitudinal axis of a catheter and/or transducer can impact timing of acoustic energy backscatter received at the ultrasound transducer. FIG. 7 illustrates a longitudinal cross-sectional view of an embodiment of a catheter 700 in an exemplary blood-filled, diseased vessel 702. The catheter 700 defines a longitudinal axis 704 and includes ultrasound transducer 706.

The vessel 702 is similar to that shown and described with respect to FIGS. 5A and 5B, except that the vessel 702 is relatively diseased as compared to the vessel of FIGS. 5A and 5B. The vessel 702 may be a vessel of a vascular system of a patient, such as a coronary artery, including a vessel wall 708 defining a vessel lumen 710 through which blood 712 flows. In addition to blood 712, the vessel lumen 710 can also include one or more plaque components 714 that have accumulated on the vessel wall 708 within the vessel lumen 710. The relatively diseased vessel 702 shown here includes more extensive plaque buildup, relative to the vessel of FIGS. 5A and 5B, defining an atherosclerotic lesion 716. The lesion 716 causes a narrowed diameter with the vessel lumen 710 at that particular location. Thus, the vessel 702 does not define a generally constant vessel lumen 710 diameter along the longitudinal direction of the vessel 702.

As shown in FIG. 7, the vessel lumen 710 can include one or more regions of disturbed blood flow 718. In the illustrated example, two regions of disturbed blood flow 718 are present adjacent the plaque buildup (e.g., atherosclerotic lesion 716). But, in other examples a single region of disturbed blood flow 718 or more than two regions of disturbed blood flow 718 can be present adjacent the plaque buildup, and/or in other locations, depending on the particular vessel. Plaque buildup, such as at the atherosclerotic lesion 716, within a vessel can act to cause the one or more regions of disturbed blood flow 718. When plaque accumulates within a portion of a vessel so as to create a non-uniform vessel diameter along such portion, blood flow is impeded upstream of this location and forced to flow in a different direction at the location of the plaque buildup (e.g., in a radial direction). This can also cause the formation of eddy flow adjacent to (e.g., immediately downstream) the plaque buildup. Therefore, where blood flow is altered by plaque components within the vessel, blood flow can be considered to be disturbed.

Disturbed blood flow can have a variety of detectable characteristics. In some instances, a region of disturbed blood flow 718 can be defined by a region within the vessel lumen 710 having non-laminar blood flow. As seen in FIG. 7, the blood 712 at disturbed blood flow regions 718 can travel in a direction that is not parallel to the vessel walls 708. In some examples, a region of disturbed blood flow can include blood flowing in a direction generally toward the catheter 700, such as the disturbed blood flow region 718 to the left (e.g., upstream) of the atherosclerotic lesion 716. This can include, in some instances, blood movement within the vessel lumen 710 in a generally radial direction relative to the longitudinal axis 704 of the catheter and/or a longitudinal axis of the ultrasound transducer 706. In many such embodiments, a region of disturbed blood flow can have a radial component (inward or outward) and a longitudinal component. In other examples, a region of disturbed blood flow can include blood flowing in a direction generally circular within the vessel lumen 710, such as the disturbed blood flow region 718 to the right (e.g., downstream) of the atherosclerotic lesion 716. Such circular flow can have portions where the blood flows in a generally radial direction relative to the longitudinal axis 704 of the catheter and/or a longitudinal axis of the ultrasound transducer 706. In regions within the vessel lumen 710, such as those spaced from the plaque buildup (e.g., atherosclerotic lesion 716), lacking disturbed blood flow, blood can flow generally laminarly. Such regions can be seen within the vessel lumen 710 in FIG. 7 where blood flows in a direction generally parallel to the vessel walls 708 (e.g., parallel to the longitudinal axis 704 of the catheter and/or a longitudinal axis of the ultrasound transducer 706).

Data vectors can be processed to detect one or more characteristics of disturbed blood flow. In some embodiments, data vectors can be processed to detect a region of disturbed blood flow by detecting a location of non-laminar blood flow within the blood-filled lumen. In some embodiments, data vectors can be processed to detect a region of disturbed blood flow by detecting a location of blood movement, within the blood-filled lumen, that is in a generally radial direction relative to the longitudinal axis of the catheter and/or ultrasound transducer. In one example, this could include detecting radial flow portions of circular blood flow. In another example, this could include detecting blood movement that has a radial component and a longitudinal component (e.g., blood movement that is at an angle between the radial and longitudinal flow directions). For instance, this could include determining whether a ratio of the radial component to the longitudinal component exceeds a predetermined threshold. In one embodiment, the predetermined threshold for the ratio of the radial component to the longitudinal component can be 50%, where the radial flow component is 50% or more in size relative to the longitudinal flow component. Depending on the desired sensitivity for detecting disturbed blood flow in particular embodiments, the predetermined threshold for the ratio can include other values in order to meet the desired sensitivity. In further embodiments, data vectors can be processed to detect a region of disturbed blood flow by detecting a location of blood movement, within the blood-filled lumen, that is not parallel to the vessel walls.

In one embodiment, data vectors can be processed to detect a region of disturbed blood flow by detecting two or more of: i) a location of non-laminar blood flow, ii) a location of blood movement(s) that is in a generally radial direction relative to the longitudinal axis of the catheter and/or ultrasound transducer and/or has a ratio of a radial component to a longitudinal component that exceeds a predetermined threshold, and iii) a location of blood movement that is not parallel to the vessel walls. Thus, by processing data vectors to detect the location of blood flow that is non-laminar, generally radial, and/or non-parallel, a region of disturbed blood flow can be identified and correlated to the location of such blood flow.

Figure 8:
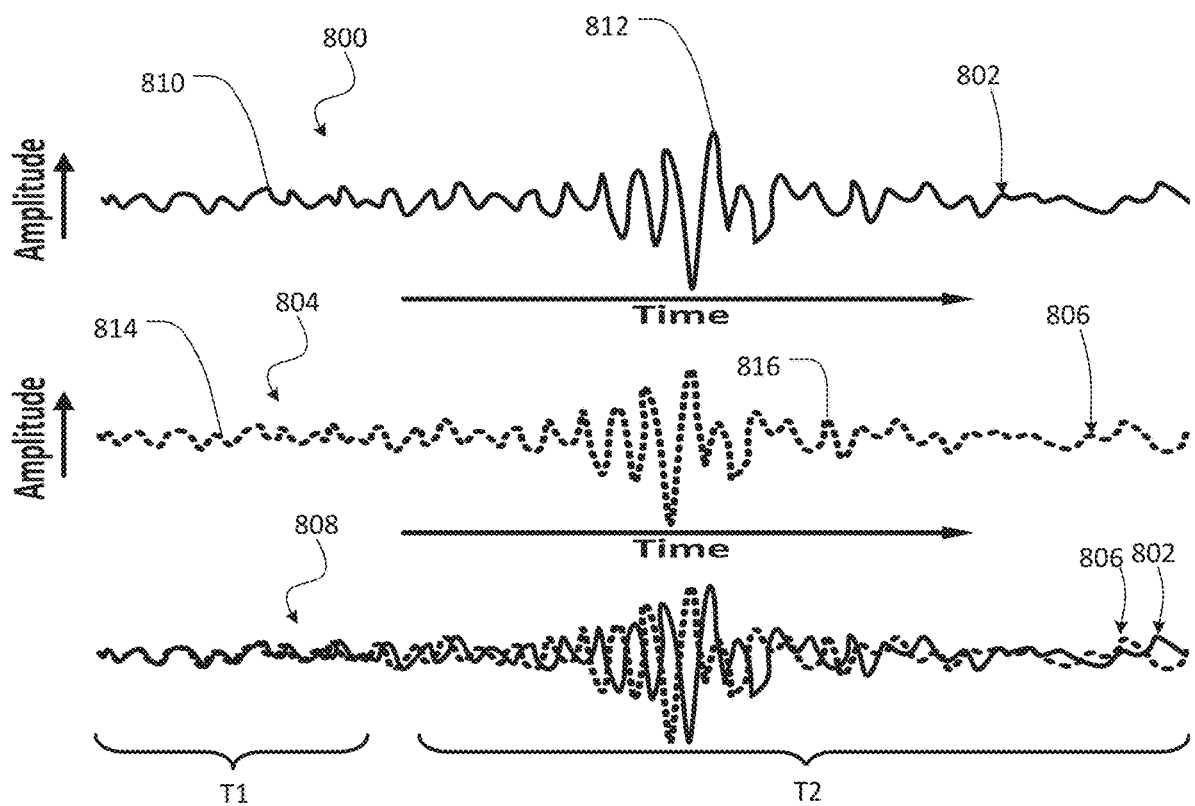
FIG. 8 shows exemplary plots of time versus amplitude for a first vector, a second vector, and an overlay of the first vector and the second vector.

A region of disturbed blood flow within a vessel lumen can impact the backscatter of acoustic energy received at the ultrasound transducer, such as by altering the timing of the backscatter of one or more data vectors relative to data vectors, or portions of the same data vector, emitted at locations without disturbed blood flow. For example, a region of disturbed blood flow can cause two data vectors to interfere (e.g., destructively interfere) with one another, as explained here with reference to FIG. 8. FIG. 8 shows an exemplary plot 800 of time versus amplitude for a first data vector 802 (solid line), an exemplary plot 804 of time versus amplitude for a second data vector 806 (dashed line), and an exemplary plot 808 of times versus amplitude for an overlay of the first data vector 802 and the second data vector 806. In some examples, the data vectors 802 and 806 can be neighboring data vectors (e.g., data vectors from consecutive ultrasound emissions to one another about the 360 degree rotation of the ultrasound transducer).

Data vectors 802 and 806 can be emitted and received via an imaging device, such as an ultrasound transducer as described previously herein. The first data vector 802 can include portions 810 and 812, while the second data vector 806 can include portions 814 and 816. Portions 810 and 814 can span a common time duration corresponding to time T1, while portion 812 and 816 can span a common time duration corresponding to time T2. The time durations T1 and T2 refer to the respective time duration, measured from emission, of each data vector 802 and 806 (although are not necessarily the same actual times, as in the case where data vectors 802 and 806 are neighboring data vectors emitted consecutively and thus at distinct times). As can be seen in the exemplary plot 808, during the time duration T1 the portions 810 and 814 include substantially similar, overlaying amplitudes with a minor level of difference between such amplitudes beginning to occur near the end of time duration T1. However, during the time duration T2 the portions 812 and 816 include differing amplitudes to a greater extent than that of portions 810 and 814. As a result, the portions 812 and 816 can create interference (e.g., destructive interference) present within the received imaging data corresponding to time duration T2.

In one example, the interference at time duration T2 between the first and second data vectors 802, 806 may result from the portion 816 of the second data vector 806 encountering a region of disturbed blood flow during time duration T2. A region of disturbed blood flow can cause interference between the first and second data vectors 802, 806 where such interference corresponds to a location of the region of disturbed blood flow. For instance, when the portion 816 of the second data vector 806 encounters the region of disturbed blood flow, the region of disturbed blood flow can cause the portion 816 to be time-shifted relative to another data vector, such as first data vector 802, and/or other portions of the second data vector 806, such as portion 814. Time-shifting of a portion of the second data vector 806 at the region of disturbed blood flow can be caused, for instance, by blood flow in the radial direction. Blood flow in the radial direction can act to cause the portion 816 to arrive sooner (e.g., with radially inwardly flowing blood) or later (e.g., with radially outwardly flowing blood) than would be the case when the data vector encounters blood flow in the parallel direction (e.g., regions without disturbed blood flow), such as with portion 812 of the first data vector 802.

The extent to which the portion 816 is time-shifted can be a function of the extent of the region of disturbed blood flow, such as the velocity and/or particular non-parallel direction of non-laminar blood flow. For example, where the region of disturbed blood flow includes blood flow in the radial direction substantially perpendicular to the longitudinal axis of the catheter (e.g., relatively large radial component) and/or transducer and at a relatively high velocity in such direction, the greater the relative time-shifting of the data vector encountering this region of disturbed blood flow will be. On the other hand, where the region of disturbed blood flow includes blood flow closer to the parallel direction than the radial direction (e.g., relatively small radial component) and at a relatively low velocity in such direction, the less the relative time-shifting of the data vector encountering this region of disturbed blood flow will be. Greater time-shifting can cause greater data vector interference, whereas less extensive time-shifting can cause less data vector interference.

In some such instances, the time-shifting of the portion 816 caused by the region of disturbed blood flow can result in an approximately half-wavelength shift of the portion 816 relative to the portion 814. When a half-wavelength shift of the portion 816 is caused, the portions 812 and 816 at time duration T2 can result in phase cancellation due to the ensuing substantially inverse amplitudes of the portions 812 and 816.

As such, in some embodiments, data vectors can be processed to detect a region of disturbed blood flow by calculating interference between first and second data vectors. This calculated interference between first and second data vectors can be used to locate a region of disturbed blood flow by correlating the location of the region of disturbed blood flow to the location of the calculated interference between the first and second data vectors.

In different embodiments, calculating interference between first and second data vectors can be accomplished in a variety of ways. In some examples, interference between first and second data vectors can be calculated by processing the first and second data vectors to ascertain a degree of phase cancellation occurs between first and second data vectors. Where the degree of phase cancellation is determined to be greater than a predetermined threshold, the location of such phase cancellation can be used to locate the region of disturbed blood flow. In other examples, interference between first and second data vectors can be calculated by processing the first and second data vectors to ascertain a half-wavelength shift of one data vector relative to another. A location where a half-wavelength shift of one data vector relative to another is determined to be present can be used to locate the region of disturbed blood flow.

In some embodiments, a region of disturbed blood flow can be detected by comparing one or more portions (e.g., portions corresponding in time duration) of respective first and second data vectors to determine an extent to which such portions differ (e.g., differ in amplitude at corresponding time durations). For instance, with reference to FIG. 8, first and second data vectors 802, 806 can be processed to determine a difference between respective portions of such data vectors 802, 806. In this example, portion 810 of the first data vector 802 can be compared with portion 814 of the second data vector 806 to determine a difference in amplitude, where portions 810 and 814 correspond to one another in time at time duration T1. Here, it can be determined that portions 810 and 814 either do not differ in amplitude or differ along time duration T1 in amplitude to an extent that is less than a predetermined threshold. When this is the case, it can be determined that portions 810 and 814 do not correspond to a location of disturbed blood flow. Similarly, portion 812 of the first data vector 802 can be compared with portion 816 of the second data vector 806 to determine a difference in amplitude, where portions 812 and 816 correspond to one another in time at time duration T2. Here, it may be determined that portions 812 and 816 differ along time duration T2 in amplitude to an extent that is equal to or greater than a predetermined threshold. When this is the case, it can be determined that portions 812 and 816 correspond to a location of disturbed blood flow.

Therefore, data vectors can be processed to detect the region of disturbed blood flow by comparing corresponding portions of data vectors to determine a difference between such portions and determining the difference to be equal to or greater than a predetermined threshold. The predetermined threshold for a difference in amplitude between data vector portions corresponding in time duration can be selected and vary depending on the desired sensitivity in detecting disturbed blood flow (e.g., a relatively lower predetermined threshold can be used in examples where a greater sensitivity for detecting disturbed blood flow is desired). For instance, in one example the predetermined threshold can be 50% such that disturbed blood flow is determined to be present when the difference in amplitude between data vector portions corresponding in time duration is equal to or greater than 50%. In another example, the predetermined threshold can be 90% such that disturbed blood flow is determined to be present when the difference in amplitude between data vector portions corresponding in time duration is equal to or greater than 90%. In some applications, a greater difference in amplitude (e.g., 90% difference) between data vector portions corresponding in time duration can correspond to a relatively greater change in image brightness to a user's eye (e.g., image becomes relatively darker at region corresponding to data vector portion) as compared to a lesser difference in amplitude (e.g., 50% difference).

Furthermore, detecting a region of disturbed blood flow by comparing corresponding portions of data vectors can include processing data vectors to ascertain a degree to which a portion of a data vector has been time-shifted. For example, the predetermined threshold used in assessing an extent to which corresponding portions of respective data vectors differ can be a predetermined degree to which a portion of one data vector is time shifted relative to another portion of the same data vector. In the illustrated example of FIG. 8, the portion 816 of the second data vector 806 is time-shifted relative to the portion 814 of the second data vector 806. Here, it may be determined that the degree to which the portion 816 is time-shifted relative to the portion 814 is equal to or greater than a predetermined degree of time-shifting. When this is the case, it can be determined that portion 816 corresponds to a location of disturbed blood flow.

The predetermined degree to which a portion of one data vector is time shifted relative to another portion of the same data vector can be selected and vary based on a desired sensitivity in detecting disturbed blood flow. In one example, the predetermined degree can be equal to or greater than a phase difference of $\pi/2$ radians (e.g., 90 degrees). In an embodiment using an intravascular ultrasound imaging system at a relatively high frequency a phase difference of $\pi/2$ radians in time can be approximately 4 nanoseconds. In another example, the predetermined degree can be equal to or greater than a phase difference of it radians (e.g., 180 degrees). In the embodiment using an intravascular ultrasound imaging system at a relatively high frequency a phase difference of it radians in time can be approximately 8 nanoseconds.

In some examples, data vectors can be processed to detect a region of disturbed blood flow by generating a speckle density of blood within the vessel. Speckle is an image artifact that commonly appears as specks in ultrasound images that are caused when structure in an imaging view is on a scale too small to be resolved by an imaging system. A density of speckle (e.g., the density of specks in the ultrasound image per unit area, such as per region of a blood-filled lumen) is directly correlated to the concentration of unresolvable structure in an object. Blood may be a cause of speckle in an ultrasound image as the content of blood (e.g., red blood cells, white blood cells, platelets) is too small to be resolved by an ultrasound transducer. Generally, speckle is considered an undesirable image artifact as it can mask small but potentially diagnostically significant imaging features.

However, despite speckle generally being considered an undesirable image artifact, some embodiments can use speckle density to detect a region of disturbed blood flow. For example, data vectors can be processed to generate a speckle density value for each of a number of regions within a blood-filled lumen. In one embodiment, a first speckle density value for a first region of the blood-filled lumen and a second speckle density value for a second region of the blood-filled lumen can be generated. The first speckle density value can be compared to the second speckle density value to calculate a difference between the first speckle density value and the second speckle density value. When the calculated difference between the first speckle density value is equal to or exceeds a predetermined threshold, the region of disturbed blood flow can be detected to correspond to the second region of the blood-filled lumen. This can be the case because a region having disturbed blood flow can have a speckle density value lower than a region without disturbed blood flow, as disturbed blood flow can generally tend to inhibit speckle that would otherwise appear in an ultrasound image (e.g. a region of disturbed blood flow can show up as predominantly dark in an ultrasound image, while a region without disturbed blood flow can show up with a number of bright specks).

In certain embodiments, two or more of the described variants for detecting a region of disturbed blood flow can be used in conjunction to detect the region of disturbed blood flow. As one example, speckle density values can be compared for respective regions in a blood-filled lumen as a way to verify that a particular region detected to have disturbed blood flow using calculated interference between data vectors is in fact a region of disturbed blood flow. Similarly, in another example, speckle density values can be compared for respective regions in a blood-filled lumen as a way to verify that a particular region detected to have disturbed blood flow using a difference between corresponding portions of distinct data vectors is in fact a region of disturbed blood flow. Likewise, in a further example, speckle density values can be compared for respective regions in a blood-filled lumen as a way to verify that a particular region detected to have disturbed blood flow using detection of blood in a generally radial direction or detection of a location of non-laminar blood flow is in fact a region of disturbed blood flow.

As described, an imaging system can be configured to process data vectors to detect one or more regions of disturbed blood flow within a vessel using one or more of the various different techniques described herein depending on the embodiment. The data vectors can also be processed to generate an intravascular image, such as an intravascular ultrasound image. To generate the intravascular image, the data vectors can be processed in a variety of ways, including performing signal processing (e.g., coherence filtering). Signal processing can be performed, in some embodiments, on a subset of data vectors within a frame. In one example, eight neighboring data vectors can be formed into a subset and undergo coherence filtering as part of the process for generating the intravascular image.

Embodiments can further include displaying the generated intravascular image (e.g., intravascular ultrasound image) with a disturbed blood flow indicator indicating the detected region of disturbed blood flow. Regions within a vessel having disturbed blood flow can generally show up as predominantly dark ("dark spots") in a generated ultrasound image, for instance due to data vector interference disrupting image data corresponding to the region. Dark spots in ultrasound images are normally considered detrimental, because dark regions can mask vessel structures and thus hamper diagnostic value of the image. In fact, extensive efforts and resources have been expended to develop various techniques to eliminate dark spots in intravascular images. However, embodiments described herein can make what has otherwise been considered detrimental valuable in assessing vessel conditions for diagnostic purposes.

It can be beneficial to indicate a region of disturbed blood flow, for example, because such region can correspond to a low endothelial shear stress at this particular location with the vessel. Low endothelial shear stress is a pro-inflammatory stimulus and, as a result, a location within a vessel experiencing low endothelial shear stress can also tend to experience plaque progression at a rate that can lead to vessel disease. Therefore, the ability to indicate disturbed blood flow may be valuable to medical personnel in predicting vulnerable plaques and/or plaque progression within a vessel as well as new clinically significant events related to the vessel.

Figure 9A:
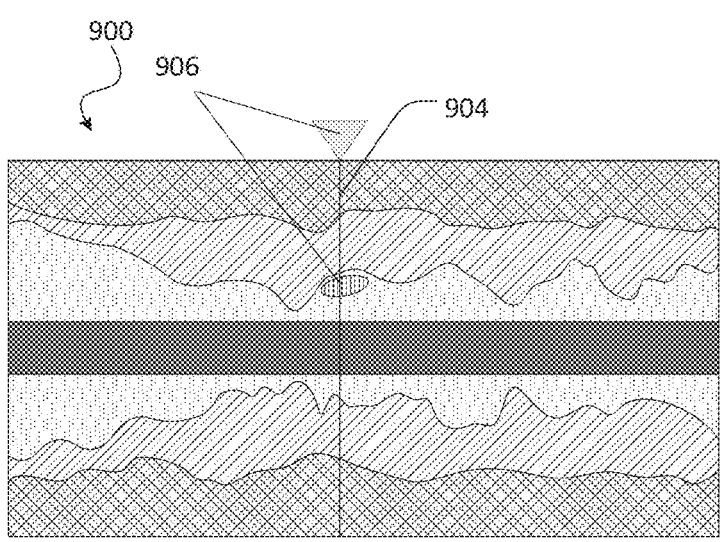
FIGS. 9A and 9B are longitudinal and transverse cross-sectional views, respectively, of embodiments of a displayed image with an indicator for a region of disturbed blood flow.
Figure 9B:
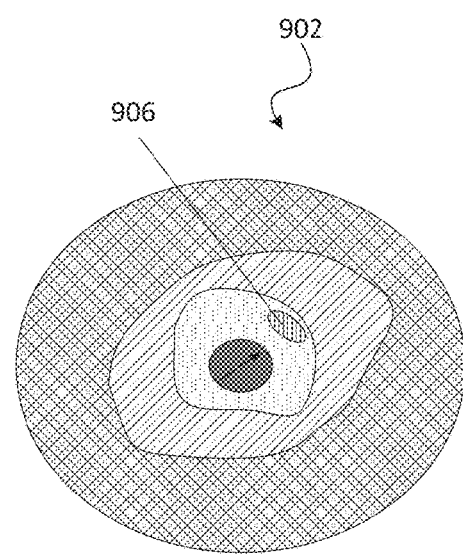

FIGS. 9A and 9B show embodiments of a displayed intravascular image, such as an intravascular ultrasound image, having a disturbed blood flow indicator. In particular, FIG. 9A shows a longitudinal view of an embodiment of a displayed intravascular image 900. FIG. 9B shows a transverse cross-sectional view of an embodiment of a displayed intravascular image 902 corresponding to a cross-section at a location along the longitudinal image 900 at demarcation 904. Such images 900 and/or 902 can, in some embodiments, be output on the image display region of the user interface on the imaging engine.

As shown, the images 900 and/or 902 can include a disturbed blood flow indicator 906. The disturbed blood flow indicator 906 can indicate a region of disturbed blood flow, such as detected in processing the data vectors. The exemplary image 900 includes two disturbed blood flow indicators 906, one indicator 906 within the vessel lumen and the other indicator 906 on a side of the vessel wall opposite the vessel lumen. In one example, such as that shown in FIG. 9A, the indicator 906 within the vessel lumen can be shaped so as to encompass the detected region of disturbed blood flow, and thus can be a dynamic shape depending on the particular size of the region of disturbed blood flow in a specific application. In such an example, the other indicator 906 in FIG. 9A on the side of the vessel wall opposite the vessel lumen can be a constant shape across applications, and thus may not vary in shape as a function of the particular detected region of disturbed blood flow. The indicator 906 in FIG. 9A on the side of the vessel wall opposite the vessel lumen can serve to illustrate to the system user that a particular longitudinal location along the vessel has been detected to have a region of disturbed blood flow. This may allow the system user to input a command to cause the transverse cross-sectional image 902 corresponding to that longitudinal location to be displayed on a same or different image display region. As such, embodiments can not only indicate but also facilitate inspection of a region of disturbed blood flow in multiple, differing views of the vessel.

The disturbed blood flow indicator 906, such as dynamic shaped indicator(s) within the vessel lumen shaped to encompass the detected region of disturbed blood flow, can be output on the displayed image 900 and/or 902 in a manner that distinguishes the indicator 906 from other portions of the displayed image 900 and/or 902. For example, in one embodiment, the indicator 906 includes a first portion of the displayed image shaded differently from a second portion of the displayed image that surrounds the first portion. The first portion could be a line (e.g., solid, dashed, etc.) shaded in a color different from the second portion of the image surrounding the first portion. In further embodiments, the area within the shaded line could also be shaded in a color similar to that of the shaded line and different from the second portion of the image surrounding the first portion, which in some examples can be similar to that shown in FIGS. 9A and 9B.

In some embodiments, the indicator 906, such as dynamic shaped indicator(s) within the vessel lumen shaped to encompass the detected region of disturbed blood flow, can be displayed on the image 900 and/or 902 to include a color gradient. For instance, the color gradient can range from a first color to a second color, where the color gradient corresponds to a degree of disturbed blood flow within the region of disturbed blood flow. In such instances, particular areas within the region of disturbed blood flow having a more extensive degree of disturbed blood flow can be shaded in a color closer to the first color, while areas within the region of disturbed blood flow having a less extensive degree of disturbed blood flow can be shaded in a color closer to the second color. Consequently, use of a color gradient in connection with indicator 906 can serve to provide a system user with an indication as to an extent of disturbed blood flow within a subset of the region of disturbed blood flow.

As will be appreciated by those skilled in the art, various other means for distinguishing the indicator 906 from other portions of the displayed image 900 and/or 902 can also be used alternatively or in conjunction with those described herein.

Figure 10:
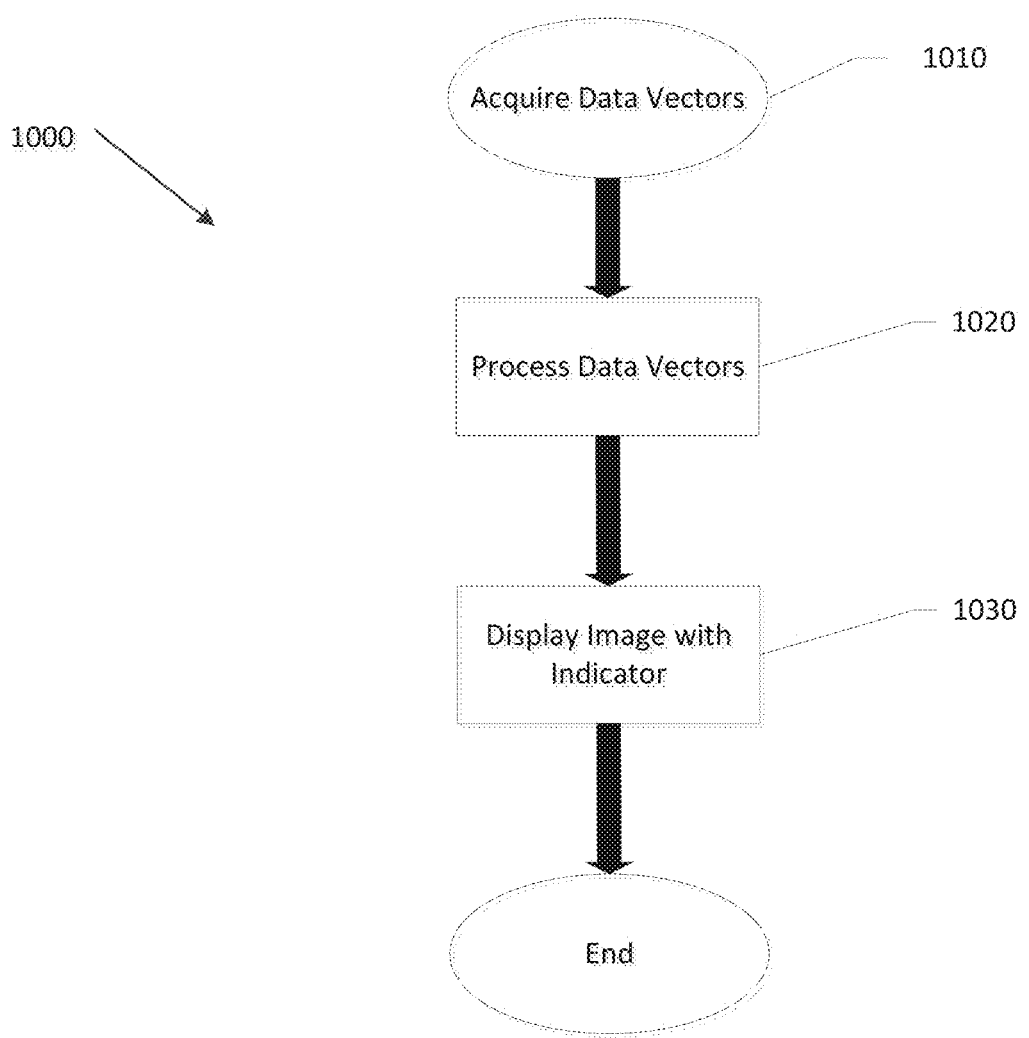
FIG. 10 is a flow diagram illustrating a method for indicating disturbed blood flow.

FIG. 10 shows a flow diagram illustrating a method 1000 for indicating disturbed blood flow. At step 1010, a plurality of data vectors can be acquired. Data vectors can be acquired, for example, in a manner similar to that described herein. One example can include emitting acoustic energy from an ultrasound transducer and receiving a backscatter of the acoustic energy at the ultrasound transducer. In this example, each data vector of the plurality of data vectors may include ultrasound data.

At step 1020, the plurality of data vectors can be processed. Processing the data vectors can include processing the data vectors to detect a region of disturbed blood flow, for example, by using techniques described herein. Processing the data vectors to detect a region of disturbed blood flow can include calculating interference between a first data vector and a second data vector. In some cases, the first and second data vectors may be neighboring data vectors. The calculated interference between the first data vector and the second data vector can include a degree of phase cancellation between the first and second data vectors. Additionally or alternatively, the calculated interference between the first data vector and the second data vector can include a half-wavelength shift of at least a portion of the first data vector.

Processing the data vectors at step 1020 to detect a region of disturbed blood flow can include, additionally or alternatively, comparing a first portion of the first data vector to a second portion of the second data vector to determine a difference between the respective first and second portions. The difference between the respective first and second portions may be equal to or greater than a predetermined threshold for a region of disturbed blood flow to be detected. In some examples, the predetermined threshold can correspond to a predetermined degree to which the second portion of the second data vector is time shifted.

Furthermore, processing the data vectors at step 1020 to detect a region of disturbed blood flow can include, additionally or alternatively, generating speckle density values for respective regions within a blood-filled lumen. The generated speckle density values can be compared to calculate a difference, and, in some embodiments, the region of disturbed blood flow can be detected to correspond to a particular region within the blood-filled lumen when the calculated speckle density difference is equal to or greater than a predetermined threshold.

Processing the data vectors at step 1020 to detect a region of disturbed blood flow can include, additionally or alternatively, detecting blood movement within the blood-filled lumen in a generally radial direction relative to the longitudinal axis of the catheter and/or ultrasound transducer. Moreover, processing the data vectors at step 1020 to detect a region of disturbed blood flow can include, additionally or alternatively, detecting non-laminar blood flow within the blood-filled lumen. Also, processing the data vectors at step 1020 to detect a region of disturbed blood flow can include, additionally or alternatively, detecting blood flow that is not generally parallel to the vessel walls.

Processing the data vectors at step 1020 can also include processing the data vectors to generate an intravascular image, such as an intravascular ultrasound image. Processing the data vectors to generate an intravascular image may include, in some examples, performing signal processing (e.g., coherence filtering) on the data vectors.

At step 1030, the intravascular image is displayed. In some embodiments, the image may be displayed on an image display region of a user interface, such as a user interface of an imaging engine. The intravascular image can be output and displayed to include a disturbed blood flow indicator indicating the region of disturbed blood flow as detected in processing the data vectors at step 1020. The disturbed blood flow indicator can, in some instances, be shaded so as to distinguish the indicator from a portion of the displayed image surrounding the indicator. The disturbed blood flow indicator may be displayed on the image to include a color gradient corresponding to a degree of disturbed blood flow within the region of disturbed blood flow.

In addition to the method 1000 described with respect to FIG. 10, embodiments can further include various imaging systems. One exemplary imaging system has a catheter assembly including an intravascular imaging device with an ultrasound transducer configured to acquire data vectors representing one or more items in an imaging view. The imaging system can further have a user interface including an image display region as well as an imaging engine in communication with both the intravascular imaging device and the user interface and comprising at least one processor. The imaging engine can be configured to receive the imaging data from the intravascular imaging device, detect, using the at least one processor, a region of disturbed blood flow in the imaging data, and generate an intravascular ultrasound image from the imaging data. The generated intravascular ultrasound image can include a disturbed blood flow indicator indicating the region of disturbed blood flow. The imaging engine can further be configured to convey to the user interface the intravascular ultrasound image having the disturbed blood flow indicator for outputting on the image display region.

Embodiments may also include a non-transitory computer-readable storage article having computer-executable instructions stored thereon to cause at least one programmable processor to receive imaging data, such as a plurality of data vectors, representing one or more items in an imaging view. Such instructions can also cause the processor to determine a region of disturbed blood flow within the blood-filled lumen based on the imaging data, for instance by using one or more techniques described herein. In addition, the instructions can cause the processor to convey an intravascular image for outputting on a display. The intravascular image can include a disturbed blood flow indicator located at the determined region of disturbed blood flow.

Various examples have been described. These and other examples are within the scope of the following claims.

The invention claimed is:

1. A method of imaging blood flow, the method comprising the steps of:
    inserting an intravascular imaging system in to a blood vessel;
    emitting acoustic energy from an ultrasound transducer and receiving a backscatter of the acoustic energy from the blood vessel at the ultrasound transducer of the intravascular imaging system;
    generating imaging data associated with a blood-filled lumen from the emitted acoustic energy from the ultrasound transducer and the received backscatter of the acoustic energy at the ultrasound transducer to acquire a plurality of data vectors including a first data vector and a second data vector, wherein each data vector of the plurality of data vectors comprises ultrasound data;
    processing the plurality of data vectors to detect a region of disturbed blood flow within the blood-filled lumen and generate an intravascular ultrasound image;
    wherein processing the plurality of data vectors comprises calculating interference between the first data vector and the second data vector, and wherein the calculated interference between the first data vector and the second data vector is used to locate the disturbed blood flow indicator at a location on the displayed intravascular ultrasound image corresponding to a location of the calculated interference between the first data vector and the second data vector; and
    displaying the intravascular ultrasound image with a disturbed blood flow indicator indicating the region of disturbed blood flow within the blood-filled lumen adjacent a first, downstream side of a lesion having flow in a different direction than flow at other another blood region within the blood-filled lumen adjacent a second, upstream side of the lesion, the disturbed blood flow indicator distinguishing the region of disturbed blood flow within the blood-filled lumen adjacent the first, downstream side of the lesion from the other another blood region within the blood-filled lumen adjacent the second, upstream side of the lesion.

2. The method of claim 1, wherein the first data vector and the second data vector are neighboring data vectors.

3. The method of claim 1, wherein the calculated interference between the first data vector and the second data vector comprises a degree of phase cancellation between the first data vector and the second data vector.

4. The method of claim 1, wherein the disturbed blood flow indicator displayed with the intravascular ultrasound image comprises a first portion of the blood-filled lumen of the displayed intravascular ultrasound image shaded differently from a second portion of the blood-filled lumen of the displayed intravascular ultrasound image surrounding the first portion.

5. The method of claim 1, wherein the disturbed blood flow indicator displayed with the intravascular ultrasound image comprises a color gradient from a first color to a second color, the color gradient corresponding to a degree of disturbed blood flow within the region of disturbed blood flow within the blood-filled lumen.

6. The method of claim 1, wherein the blood-filled lumen comprises a coronary artery and a plaque buildup defines the lesion, and wherein the region of disturbed blood flow within the blood-filled lumen is located at a location within the coronary artery adjacent the first, downstream side of the plaque buildup in the coronary artery.

7. The method of claim 1, wherein displaying the intravascular ultrasound image comprises:
    displaying a longitudinal intravascular ultrasound image with a first disturbed blood flow indicator indicating the region of disturbed blood flow within the blood-filled lumen of the longitudinal intravascular ultrasound image; and
    displaying a cross-sectional intravascular ultrasound image with a second disturbed blood flow indicator indicating the region of disturbed blood flow within the blood-filled lumen of the cross-sectional intravascular ultrasound image.

8. The method of claim 1, wherein the image data is generated when a blood displacement fluid is present within the blood-filled lumen.

9. The method of claim 1, wherein a plaque buildup defines the lesion, and wherein the disturbed blood flow indicator is displayed offset from a longitudinal axis of the blood-filled lumen in a longitudinal direction toward the plaque buildup.

* * * * *